United States Patent
Benter et al.

(10) Patent No.: US 9,228,926 B2
(45) Date of Patent: Jan. 5, 2016

(54) CHEMICAL IONIZATION WITH REACTANT ION FORMATION AT ATMOSPHERIC PRESSURE IN A MASS SPECTROMETER

(71) Applicant: Bruker Daltonik GmbH, Bremen (DE)

(72) Inventors: Thorsten Benter, Haan (DE); Sonja Klee, Wuppertal (DE)

(*) Notice: Subject to any disclaimer, the term of this patent is extended or adjusted under 35 U.S.C. 154(b) by 0 days.

(21) Appl. No.: 14/259,318

(22) Filed: Apr. 23, 2014

(65) Prior Publication Data

US 2014/0314660 A1 Oct. 23, 2014

(30) Foreign Application Priority Data

Apr. 23, 2013 (DE) .................... 10 2013 006 971

(51) Int. Cl.
*G01N 1/44* (2006.01)
*H01J 49/14* (2006.01)
*H01J 49/16* (2006.01)

(52) U.S. Cl.
CPC .............. *G01N 1/44* (2013.01); *H01J 49/145* (2013.01); *H01J 49/168* (2013.01)

(58) Field of Classification Search
USPC .............. 250/281, 282, 288, 324, 337, 423 F, 250/423 P, 423 R, 427; 423/659; 436/174; 422/186, 186.4
See application file for complete search history.

(56) References Cited

U.S. PATENT DOCUMENTS 5,847,386 A * 12/1998 Thomson et al. ............. 250/288
8,481,927 B2 7/2013 Franzen et al.
2005/0199799 A1 * 9/2005 Takada et al. ................. 250/288
2007/0092964 A1 * 4/2007 Wagner et al. ............. 435/287.2
2008/0203303 A1 8/2008 Lloyd et al.
2008/0277272 A1 * 11/2008 Pierce et al. .................. 204/164
2011/0039350 A1 2/2011 Franzen
2012/0312980 A1 * 12/2012 Whitehouse ................. 250/282

FOREIGN PATENT DOCUMENTS

WO 2009066087 A2 5/2009

OTHER PUBLICATIONS

Shirai, Naoki et al., Atmospheric negative corona discharge using Taylor cone as a liquid cathode, Japanese Journal of Applied Physics 53, Jan. 2014, p. 026001-1 to 026006.
Shirai, Naoki et al., Atmospheric Negative Corona Discharge Observed at Tip of Taylor Cone Using PVA Solution, IEEE Transactions on Plasma Science, vol. 39, No. 11, Nov. 2011, pp. 2210-2211.

* cited by examiner

*Primary Examiner* — Phillip A Johnston
*Assistant Examiner* — Hsien Tsai
(74) *Attorney, Agent, or Firm* — Benoit & Cote, Inc.

(57) ABSTRACT

The invention relates to the production of water cluster ions ("hydronium clusters") at atmospheric pressure for the chemical ionization of analyte molecules. It is proposed that a corona discharge at the Taylor cone of an aqueous liquid, preferably pure or slightly acidified pure water, is used instead of corona discharges on metal tips, which have been the usual method up to now. The hydronium clusters of the form $[H(H_2O)_n]^+$ can be produced in a discharge chamber, which is separate from the ionization chamber, and introduced into the ionization chamber through a capillary. In the ionization chamber, the hydronium clusters can be heated and reduced in size by means of electrical acceleration and gas collisions, and thus made more reactive in order that analyte molecules of low proton affinity can also be ionized.

20 Claims, 1 Drawing Sheet

CHEMICAL IONIZATION WITH REACTANT ION FORMATION AT ATMOSPHERIC PRESSURE IN A MASS SPECTROMETER

BACKGROUND OF THE INVENTION

1. Field of the Invention

The invention relates to the generation of water cluster ions (hydronium clusters) at atmospheric pressure for the chemical ionization of analyte molecules in a mass spectrometer.

2. Description of the Related Art

In this document, the term "hydronium" refers to the cation $H_3O^+$. The literature is somewhat inconsistent in that this cation is sometimes called simply "hydronium", but the term "hydronium ion" is also used. The complexes with further water molecules are called "hydronium clusters" here; these are always positively charged.

Atmospheric pressure chemical ionization (APCI) usually takes place in an ionization chamber in which a corona discharge burns at a metal tip due to the application of a high voltage of several kilovolts. The analyte molecules which are to be ionized are introduced into the ionization chamber. The corona discharge usually burns in a nitrogen atmosphere, creating nitrogen ions primarily. Hydronium clusters of the form $[H(H_2O)_n]^+$ are created from the nitrogen ions on a microsecond time scale due to water being unavoidably present in at least ppm concentrations. These clusters are able to ionize the analyte molecules by means of a subsequent complex proton transfer. In equilibrium at room temperature and ambient pressure, the hydronium clusters have a broad distribution of cluster size n, mainly with $3<n<9$, where the protonation force of the clusters is very small for large n due to low acidity; for very small n the protonation force is large due to high acidity. The distribution of the cluster size depends on the local pressure and the local temperature, but also on the distance from the metal tip and the concentration of the water since, initially, the hydronium ($H_3O^+$) is formed near the tip, but surrounds itself with further water molecules as it migrates away from the tip to the outside. The lower the water concentration, the further to the outside the cluster formation takes place, and the larger is the space in which an analyte molecule of a specific proton affinity can be ionized. In order to maintain uniform ionization of analyte molecules for quantitative analyses, it is necessary to have good control of the water concentration.

Chemical ionization by hydronium clusters is a complex process which does not consist simply of a proton transfer to the analyte molecule, but can also run through phases where an analyte molecule combines with a hydronium cluster with subsequent loss of neutral water molecules. The intermediate stages can be understood as protonated analyte ions with a solvate sheath. The water molecules can leave the complex if the analyte molecule has a sufficiently high internal temperature. The release of the water molecules causes the internal temperature to fall. The removal of the solvate sheath ("desolvation") can be assisted in the known way by collisions with ambient gas, which cause heating. In this way it is possible, to a lesser extent, to also ionize analyte molecules of lower proton affinity with larger hydronium clusters, i.e. of higher proton affinity, although this is not energetically possible by the direct route of a proton transfer.

In order to facilitate the protonation, however, it may be appropriate to first decompose the hydronium clusters by collisional heating so that, most importantly, the $H_3O^+$ and $H_5O_2^+$ ions are again available for the protonation. The collisional heating consists in drawing the hydronium cluster ions through a suitable gas with the aid of an electric drawing field at a suitable pressure so that they absorb energy from a large number of collisions. This technique has led to a separate type of mass spectrometry which is called PTR-MS and is used especially to measure organic trace impurities in ambient air (PTR=proton transfer reaction). PTR is understood more restrictively to be a special type of chemical ionization where hydronium clusters are reduced in size by heating collisions, such as in a linear drift tube, thus making it possible to also quantitatively ionize low-molecular substances of relatively low proton affinity. In PTR-MS, the hydronium clusters are produced by hollow cathode discharges at low pressures of water being fed in.

Outside of the specialized PTR-MS, there are two designs of APCI ion sources for mass spectrometers of a more general type. In the first design, the analyte molecules are introduced in a gas, for example from a gas chromatograph. The molecules are usually relatively small, vaporizable analyte molecules with molecular masses below 500 daltons. The feeding gas is essentially dry, with a water content of a few ppm (parts per million) to a few hundred ppm. Since the proton affinities of these analyte molecules are usually not very high, the aim is to keep the hydronium clusters as small as possible, i.e., to maintain a low yet constant water concentration in the ionization chamber with the corona discharge. This is difficult. Moreover, the corona discharge has a tendency to also form reactive compounds, such as ozone $O_3$ and OH radicals, which can lead to oxidative changes of the analyte molecules. Furthermore, some of the analyte ions always decompose in the corona discharge, which leads to undesirable fragment ions in the mass spectra. It is therefore advantageous to spatially separate the formation of the reactant ions and the chemical ionization of the analyte molecules, as has already been proposed in the patent specification DE 10 2009 037 716 B4 (T. Benter et al.; corresponding to US 2011/0039350 A1 and GB 2 473 106 A).

The second type of APCI ion source is designed to ionize analyte molecules which are brought into the gas phase by spraying, for example thermospraying or spraying by a gas jet, via the drying of the spray droplets. This also includes the post-ionization of analyte molecules which are not at all ionized in electrospray ion sources, or only to a small extent. Electrospray ion sources are used mainly for the ionization of biological macromolecules such as peptides and proteins. These can generally be protonated efficiently. There are exceptions, however, which can be post-ionized by Cl. Such a post-ionization is described in US 2008/0173809 A1, for example. Since the spray liquids usually contain water, there is a high concentration of water in the ionization chamber; but the usually chaotic gas flows and gas vortices in the ionization chamber do not produce a well-controlled chemical ionization.

In view of the foregoing, there is a need to produce hydronium clusters in a simple, stable and well-controlled way with the facility to adjust the size distribution of the clusters so that they can be effectively used as reactant ions for the chemical ionization of analyte molecules.

SUMMARY OF THE INVENTION

Hydronium clusters are produced using a corona discharge at the Taylor cone of an aqueous liquid, preferably pure or slightly acidified water, at the tip of a fine capillary in a small discharge chamber at atmospheric pressure, separate from the feed-in of the analyte molecules. After generation, the hydronium clusters are brought together with the analyte molecules at a different location. The ionization can then be carried out in a region and at a gas pressure where, if required, a desired distribution of the hydronium clusters can be set up by collisional heating.

Instead of corona discharges on metal tips, which have been the usual method up to now to generate reactant ions for chemical ionization, this invention uses a corona discharge at the Taylor cone of an aqueous liquid, preferably pure or slightly acidified pure water, in a closed discharge chamber. The water cluster ions ("hydronium clusters") of the form $[H(H_2O)_n]^+$ can be introduced into a separate ionization region through a capillary, for example. In the ionization region, the hydronium clusters can be heated and reduced in size by means of gas collisions induced by electrical acceleration so that analyte molecules of low proton affinity can also be ionized.

The use of a "liquid" electrode at which the corona discharge is formed has the particular advantage over conventional metal electrodes in that there is no wear and tear, since the liquid is continuously supplied afresh. This characteristic particularly means that a reactant ion source operated in such a way has an advantageously long lifetime and operating time. When a "Taylor cone" is mentioned here, this also includes the formation of similar forms which can be created by the effect of the discharge plasma.

"Pure water" here means de-ionized, distilled or double distilled water (aqua bidestillata); this can, however, contain admixtures such as heavy water. Water of this purity can, for example, meet the specifications of "highly purified water" according to the European Pharmacopeia: (i) conductivity≤1.1 µS/cm at 20° C., (ii) total organic carbons≤0.5 mg/l and (iii) nitrates≤0.2 mg/l. More suitable is pure water with a conductivity of <0.5 µS/cm, however. "Slightly acidified water" here means pure water to which a small quantity of any organic or inorganic acid has been added to assist a stably burning discharge. It is preferable to use an inorganic acid, such as hydrochloric acid or nitrous acid, so that no organic compounds such as amino acids can form in the plasma of the discharge. Since nitrous acid contains only hydrogen, nitrogen and oxygen, no products can form which could not form from the nitrogen and pure water fed in.

If clean nitrogen is fed into the small discharge chamber and pure or slightly acidified water is fed in via an electrically insulated capillary, and a voltage of three to four kilovolts is applied to the capillary, a Taylor cone forms at the capillary tip and an electrospray process takes place on the surface of the water. If the voltage is increased, the electrospraying stops and a stable corona discharge with a bluish color burns at the tip of the Taylor cone. The corona discharge burns in the nitrogen and nitrogen ions form, but secondary reactions cause them to turn almost immediately into hydronium $H_3O^+$. It is also possible for water molecules to be ionized directly. Since the chamber has a high water vapor content, or is even almost saturated with water vapor in some embodiments, hydronium clusters of the form $[H(H_2O)_n]^+$ are created with a cluster size distribution n between n=5 and n=9.

These hydronium clusters can be drawn off from the small chamber, through a fine capillary, for example. The drawing-off capillary can then, for example, merge with a second capillary, in which analyte molecules in a guide gas are fed in. After the merger, the capillary can lead to a first vacuum stage of a vacuum system, while the analyte molecules and hydronium clusters already mix intensively in the capillary. After exiting into the vacuum stage, a supersonic jet is formed over several millimeters, but disintegrates after a few millimeters due to the friction with the ambient gas. In the reheated gas containing analyte molecules and hydronium clusters, the hydronium clusters can be collisionally heated over several centimeters by an electric voltage and decomposed so that they ionize the analyte molecules with a high yield. The analyte molecules can then be collected, for example by means of an ion funnel or other suitable type of ion guide, and introduced into the mass analyzer.

It is also possible for the analyte molecules which are merged with the hydronium clusters to already be partially ionized, for example by electrospraying.

Deuterated water can be used in specific embodiments, for example in order to investigate hydrogen/deuterium (H/D) exchange processes.

Figure 1:
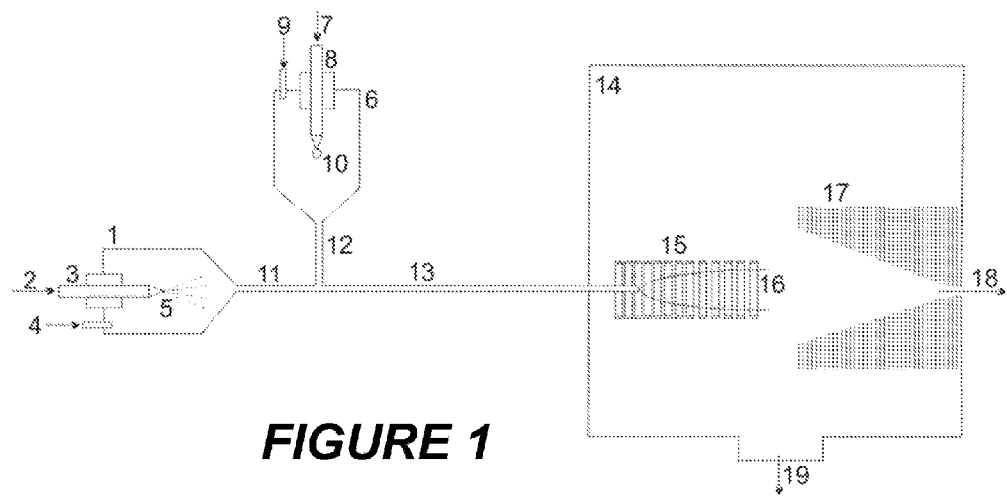
FIG. 1 is a very schematic example of an overall arrangement with an electrospray ion source (1), a discharge cell (6) for producing hydronium clusters, capillaries (11, 12, 13) for introducing the ions into the vacuum chamber (14), a field-generating envelope (15) for the gas jet (16) in the vacuum, and an ion funnel (17) for transmitting (18) the ions to a mass analyzer. The vacuum chamber (14) is evacuated in direction (19).

The discharge chamber (6) for producing the hydronium clusters has a feed-in (9) for pure nitrogen and an insulated capillary (8), made of quartz, for example, into which a small amount of pure or slightly acidified pure water (7) is pumped. When a high voltage of a few kilovolts is applied, a luminous corona discharge (10) is generated at the tip of a Taylor cone.

The electrospray ion source (1) has a feed-in (4) for a heated guide gas, also pure nitrogen, for example, and a capillary (3) through which the spray liquid (2) is introduced. The liquid at the Taylor cone is sprayed by means of a voltage of a few kilovolts; the tiny droplets dry in the heated guide gas, leaving analyte ions behind. Not all types of analyte molecule are ionized in this way.

Figure 2:
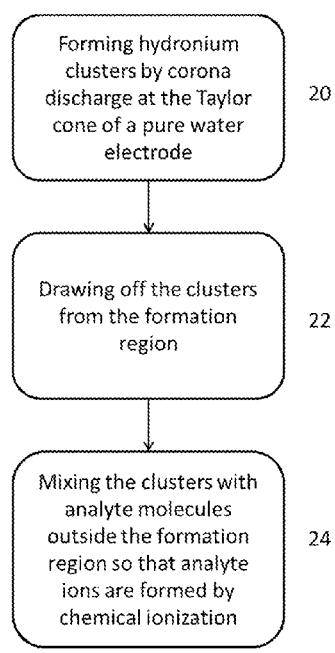

FIG. 2 is flow chart of a method according to principles of the invention.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

Hydronium clusters $[H(H_2O)_n]^+$ are produced in a small discharge chamber at atmospheric pressure, separate from the feeding in of the analyte molecules; and the hydronium clusters are brought together with the analyte molecules at a location outside the discharge chamber. In order to achieve a pure mixture of a guide gas, preferably pure nitrogen, with hydronium clusters, it is preferable to use a corona discharge at the Taylor cone of pure water at the tip of a fine capillary with an inside diameter of around 0.2 to 0.8 millimeters. Neither ozone nor ions of impurities or synthesis products are produced in this process; reactive neutral radicals have sufficient time to finish reacting. Most importantly, no analyte molecules can be chemically changed in the discharge region. The ionization can then be carried out in a region and at a gas pressure where, if desired, collisional heating can be used to set up a desired distribution of the hydronium clusters.

It has recently been reported that a corona discharge can burn at the tip of the Taylor cone of a water-based operating fluid; cf. the publication "Atmospheric negative corona discharge using a Taylor cone as liquid electrode" (R. Sekine et al., American Physical Society, 65th Annual Gaseous Electronics Conference, Oct. 22-26, 2012). In this publication, admixtures were added to the water to reduce the surface tension and increase the viscosity and conductivity. It was not possible to ignite a corona discharge with pure water. The publication states: "The liquid with high surface tension such as pure water could not form a Taylor cone". The corona discharge did not burn at the tip of the Taylor cone but around a drawn out filament of liquid. However, the authors only investigate the behavior of the corona discharge under different operating conditions. Neither technical applications for the described corona discharge with a liquid electrode, nor an analysis of the resulting gaseous compounds are described or proposed.

In contrast to the publication by Sekine et al., pure or only slightly acidified water is preferred here for producing hydronium clusters in order to avoid synthesizing any substances which could interfere during the analysis of the analyte substances. In particular there should be no organic substances in the pure water, and the nitrogen fed in must not contain any $CO_2$. It has been known for years that energetically stable organic substances, first and foremost amino acids, are formed by electrical discharges in gas mixtures which contain nitrogen, water and carbon dioxide, and these organic substances would have a particularly interfering effect during the analysis of peptides and proteins. Contrary to the results obtained by Sekine et al., if a very fine capillary (8) with an outside diameter of only around one millimeter is used, it is indeed possible to produce a Taylor cone at whose tip a corona discharge (10) burns without a water jet being formed. The preference for pure or only slightly acidified water should not limit the invention, however; it may indeed be useful for specific analytical tasks to add small doses of foreign substances to the water.

As is depicted in FIG. 1, a small flow of clean nitrogen is fed into the small discharge chamber (6) through the feed-in (9). The discharge chamber (6) tapers down to a preferably metal funnel which runs into a capillary (12). A small flow (7) of pure water, only a few nanoliters per minute, enters through the electrically insulated capillary (8), preferably controlled by a nano-pump. If a voltage of three to four kilovolts is applied between the housing of the discharge chamber (6) and the capillary (8), a Taylor cone forms at the capillary tip and an electrospray process takes place on the surface of the water. If the voltage is increased, the electrospraying stops and a stable corona discharge (10) with a bluish color burns at the tip of the Taylor cone. The corona discharge (10) burns in the nitrogen and produces mainly nitrogen ions of the form $N_2^{.+}$. These immediately react further to hydronium ions $H_3O^+$, however:

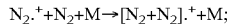

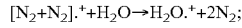

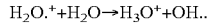

On the other hand, water molecules can also be ionized directly in the discharge:

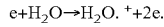

M here is an arbitrary collision partner which serves to remove excess energy. Since the discharge chamber (6) has a high water vapor content, and is even almost saturated with water vapor in some embodiments, hydronium clusters of the form $[H(H_2O)_n]^+$ are created on a microsecond time scale with a broad distribution n of the cluster sizes $5 < n < 9$.

The corona discharge burns with outstanding stability and can be maintained over days or weeks, since no contamination occurs in the discharge chamber, and the tip where the corona discharge burns continually renews itself.

Guided by nitrogen and water vapor, the hydronium clusters can be drawn off from the small discharge chamber via the fine capillary (12) at the end of the metal funnel. The drawing off capillary (12) can be several centimeters long, preferably with an inside diameter of 0.4 to 0.7 millimeters. This capillary can then, for example, be merged with a second capillary (11) of similar dimensions, which feeds in the analyte molecules in a further guide gas. The analyte molecules can originate from any device, for example directly from a gas chromatograph or, as shown in FIG. 1, from an electrospray ion source (1). Thus, the method can in particular also be used to post-ionize the uncharged molecules which are produced in an electrospray process.

After the merger of the two capillaries (11) and (12), the continuing capillary (13), which can have a usual length of 10 to 20 centimeters and a usual inside diameter of 0.4 to 0.7 millimeters, for example, can lead into a first vacuum stage (14) of the vacuum system of a mass spectrometer, while the analyte molecules and the hydronium clusters already mix intensively in the capillary (13). The suction of the vacuum provides the gas flow in the capillaries (11), (12) and (13), and recent findings indicate it is highly probable that fully turbulent flows ensue in all three capillaries. The strength of flow in the two capillaries (11) and (12) for analyte molecules and hydronium clusters depends on the flow resistances of the capillaries. The capillaries can be made of metal, or of glass or similar materials. Insulating capillaries can preferably be provided with a high-resistance layer in order to prevent the interior surface from becoming charged. The capillaries have an astonishingly high transfer yield for ions, although the most recent findings indicate it is highly probable that the flow inside them is fully turbulent.

After the gas containing the analyte molecules, water vapor and hydronium clusters leaves the capillary (13) and enters the vacuum stage (14), a supersonic jet is generated over several millimeters, in which strong cooling leads again to an increase in the size of the hydronium clusters. The supersonic jet disintegrates after only a few millimeters, however, due to the friction with the ambient gas; the gas reheats in this process, but still forms a strong flow in the direction of the out-flow in the shape of a lobe (16). The ambient pressure is usually a few hectopascal; it depends in particular on the suction power of the pump (19) for this vacuum stage and the quantity of gas fed in through the capillary (13).

In the reheated gas jet (16), the hydronium clusters can be collisionally heated in the guide gas over a few centimeters by an electric voltage and decomposed so that they ionize the analyte molecules if they are not yet ionized. The gas lobe can be surrounded by a tubular enveloping device (15) which keeps the gas together over a distance of a few centimeters and only then allows a radial expansion. The envelope (15) can initially be closed so as to be almost gastight near the outflow opening of the capillary (13), and open up more and more further away from the outflow; it can in particular carry the electrodes for generating the electric accelerating field to heat the hydronium clusters.

The electric field must be strong enough that the hydronium clusters are reduced in size sufficiently but the analyte ions produced (or already present) are not fragmented. This is usually relatively easy to achieve because the binding energies of the water in the hydronium cluster are relatively low (~1 to ~3 eV), lower than the energies of the covalent bonds in the analyte molecules (>5 eV). The field can be a DC field, which transports the ions away from the entrance capillary (13) into the open vacuum chamber (14); but it can also be an AC field, in particular an asymmetric AC field, which strengthens the effect of the cluster disintegration but again transports the ions away from the inlet capillary.

The voltage which generates the field should be adjustable in order to satisfy different analytical requirements. The adjustment of the field-generating voltage can be used, for example, to selectively ionize some substance classes in order to distinguish them from other classes of substance which are not ionized at this voltage. It is also possible to avoid fragmentation of sensitive molecular ions, in particular ions of molecular complexes, by using suitable settings, if necessary to the detriment of the sensitivity.

The ions enter the vacuum chamber (14) through the open end of the envelope (15). This means both the analyte ions and the remaining hydronium ions. The ions can then be collected by an RF ion funnel (17), for example, and fed to the mass analyzer in the direction (18). In the RF ion funnel (17), the analyte ions are freed of their solvate sheath in the known way by the oscillating motions in the RF field. Instead of the RF ion funnel, it is also possible to use other types of ion guide, such as RF ring diaphragm systems, multipole rod systems and others.

The schematic shown in FIG. 1, in which the analyte molecules are introduced into the gas phase by electrospraying, is only intended as an example of the integration of the hydronium cluster source into a mass spectrometric ion source. The hydronium clusters can be merged with analyte molecules from very different origins. The analyte molecules can be transported to this location with a guide gas directly from reaction chambers or gas chromatographs. They can originate from the spraying of the liquid from a capillary electrophoresis device, a liquid chromatograph or a nano-pump. In the spraying device, the liquids can be sprayed to form droplets by thermospraying, gas spraying or electrospraying, for example, and subsequently dried.

The analyte molecules and hydronium clusters can be mixed in capillaries, as is depicted in FIG. 1, or in chambers designed especially for this purpose.

The enveloping device (15) can also be omitted for some analytical tasks, for example. The ionization can then be carried out in the RF ion funnel (17), for example. Here too, when the RF voltage is set correctly, a reduction in the size of the hydronium clusters and an effective ionization of the analyte molecules can be achieved.

The analyte molecules which are merged with the hydronium clusters can, of course, already be partially ionized, for example by electrospraying.

FIG. 2 shows a flow chart of an exemplary method. Step (20) includes forming hydronium clusters by corona discharge at the Taylor cone of a pure water electrode. The method continues with step (22) including drawing off the clusters from the formation region of the hydronium clusters. Finally, step (24) includes mixing the clusters with the analyte molecules outside the formation region, whereby analyte ions are formed from the analyte molecules via chemical ionization.

Different aspects of the invention have been elucidated above. It will be understood, however, that various aspects or details of the invention may be changed, or that different aspects disclosed in conjunction with different embodiments of the invention may be readily combined if practicable, without departing from the scope of the invention. Furthermore, the foregoing description is for the purpose of illustration only, and not for the purpose of limiting the invention which is defined solely by the appended claims.

The invention claimed is:

1. A method for the chemical ionization of gaseous analyte molecules, wherein hydronium clusters are formed in a discharge chamber by a corona discharge using a Taylor cone as an electrode of pure or slightly acidified pure water, and these clusters are drawn off from the discharge chamber in a guide gas and mixed with the analyte molecules outside the discharge chamber so that the analyte molecules may undergo chemical ionization.

2. The method according to claim 1, wherein the drawing off of the hydronium clusters, the feeding in of the analyte molecules, and the mixing are each carried out by guide gases in capillaries.

3. The method according to claim 1, wherein the mixture of analyte molecules and hydronium clusters is fed together with guide gas through a capillary into a first stage of a vacuum system.

4. The method according to claim 2, wherein the capillaries are made of metal or glass.

5. The method according to claim 2, wherein the capillaries are electrically insulating and further provided with a high-resistance layer in order to prevent an interior surface from becoming charged.

6. The method according to claim 3, wherein the hydronium clusters are accelerated by an electric voltage in the first stage of the vacuum system and heated by collisions with the guide gas so that they can protonate the analyte molecules effectively.

7. The method according to claim 6, wherein the electric voltage is adjustable.

8. The method according to claim 6, wherein the guide gas, the analyte molecules and the hydronium clusters are kept together for at least a few centimeters by an envelope in the first stage of the vacuum system in order to allow effective chemical ionization of the analyte molecules.

9. The method according to claim 3, wherein, upon exiting into the first vacuum stage, a supersonic jet is formed from the mixture persisting over a distance of several millimeters and then disintegrating due to the friction with an ambient gas.

10. The method according to claim 3, wherein the analyte ions are collected by an RF ion funnel or other ion guide and introduced into a mass spectrometer.

11. The method according to claim 1, wherein the analyte molecules which are mixed with the hydronium clusters are already partially ionized, and the remaining uncharged analyte molecules are post-ionized by reaction with the clusters.

12. The method according to claim 1, wherein the pure water is at least partially deuterated.

13. The method according to claim 1, wherein a small dose of at least one other substance is admixed to the pure water.

14. The method according to claim 1, wherein the clusters take the form of $[H(H_2O)_n]^+$.

15. The method according to claim 14, wherein the hydronium clusters of the form $[H(H_2O)_n]^+$ are created with a predominant cluster size distribution n between n=5 and n=9.

16. The method according to claim 1, wherein the pure water comprises one of de-ionized, distilled and double distilled water (aqua bidestillata).

17. The method according to claim 1, wherein slightly acidified water comprises pure water to which a small quantity of an organic or inorganic acid has been added to assist a stably burning discharge.

18. The method according to claim 17, wherein the inorganic acid is one of hydrochloric acid and nitrous acid so that no organic compounds such as amino acids can form in the plasma of the discharge.

19. The method according to claim 1, wherein the guide gas comprises pure nitrogen $N_2$.

20. The method according to claim 1, wherein the analyte molecules originate from the spraying of a liquid from one of a capillary electrophoresis device, a liquid chromatograph and a nano-pump.

* * * * *